US012759092B2

(12) United States Patent
Furrer et al.

(10) Patent No.: US 12,759,092 B2
(45) Date of Patent: Oct. 13, 2026

(54) PREDICTIVE OPTIMIZATION AND CONTROL FOR FUSION WELDING OF METALS

(71) Applicant: RTX Corporation, Farmington, CT (US)

(72) Inventors: David U. Furrer, Marlborough, CT (US); Sergei F. Burlatsky, West Hartford, CT (US)

(73) Assignee: RTX Corporation, Farmington, CT (US)

(*) Notice: Subject to any disclaimer, the term of this patent is extended or adjusted under 35 U.S.C. 154(b) by 721 days.

(21) Appl. No.: 18/126,596

(22) Filed: Mar. 27, 2023

(65) Prior Publication Data

US 2023/0321763 A1 Oct. 12, 2023

Related U.S. Application Data

(60) Provisional application No. 63/324,294, filed on Mar. 28, 2022.

(51) Int. Cl.

| | |
|---|---|
| ***B23K 31/12*** | (2006.01) |
| ***G01N 33/207*** | (2019.01) |
| *G06F 30/20* | (2020.01) |

(52) U.S. Cl.

CPC ......... *B23K 31/125* (2013.01); *G01N 33/207* (2019.01); *G06F 30/20* (2020.01)

(58) Field of Classification Search

CPC ........ B23K 31/00; B23K 31/02; B23K 31/12; B23K 31/125; B23K 26/00; B23K 26/20; B23K 26/21; B23K 26/24; B23K 26/32; G01N 33/2045; G01N 33/207; G06F 30/20

See application file for complete search history.

(56) References Cited

U.S. PATENT DOCUMENTS

| | | | |
|---|---|---|---|
| 8,498,728 B2 | 7/2013 | Conrardy et al. | |
| 8,910,850 B2 | 12/2014 | Michaut | |
| 10,234,848 B2 | 3/2019 | Mehr et al. | |
| 11,229,973 B2 | 1/2022 | Haug et al. | |
| 2013/0056524 A1* | 3/2013 | Michaut ................ | B23K 31/02 228/102 |

(Continued)

FOREIGN PATENT DOCUMENTS

| | | |
|---|---|---|
| CN | 113500323 A | 10/2021 |
| EP | 3242767 B1 | 1/2019 |

(Continued)

OTHER PUBLICATIONS

European Serach Report dated Aug. 7, 2023; EP Application No. 23164801.5; 9 pages.

(Continued)

*Primary Examiner* — Hung D Nguyen

(74) *Attorney, Agent, or Firm* — CANTOR COLBURN LLP

(57) ABSTRACT

A method includes receiving weld data about a weld, and analyzing, using a physics-based model, the weld data to predict a formation of a defect in the weld. The method further includes providing feedback to enable process optimization during a design stage or active control during welding to control a welding machine to correct for and eliminate the formation of the defect in the weld.

16 Claims, 8 Drawing Sheets

(56) References Cited

U.S. PATENT DOCUMENTS

| | | | | |
|---|---|---|---|---|
| 2016/0193680 | A1 * | 7/2016 | Pesme .................. | B23K 31/125 219/130.01 |
| 2020/0096970 | A1 * | 3/2020 | Mehr ................. | G05B 19/4099 |
| 2020/0130108 | A1 | 4/2020 | Duan et al. | |
| 2020/0254562 | A1 * | 8/2020 | Brescoe ............. | G02B 6/02042 |
| 2023/0040619 | A1 * | 2/2023 | Di Stefano .......... | B23K 31/125 |

FOREIGN PATENT DOCUMENTS

| | | | |
|---|---|---|---|
| WO | 2011144262 | A1 | 11/2011 |
| WO | 2012029010 | A1 | 3/2012 |
| WO | 2020167588 | A1 | 8/2020 |
| WO | 2021152344 | A1 | 8/2021 |

OTHER PUBLICATIONS

Search Report issued in European Patent Application No. 23164801.5; Date of Mailing Apr. 3, 2025 (4 pages).

* cited by examiner

302

500

| Critical Models and Criterion within Wleding Model | | |
|---|---|---|
| **Model / Criterion** | **Function** | **Output** |
| Marangoni-based Flow Model | Prediction of flow and temperature profile in melt pool | Local temperature in melt pool |
| Keyhole Onset Criterion | Definition of when keyhole features form | Criterion value for keyhole formation |
| Keyhole Stability Criterion | Definition of when keyhole is stable | Criterion value for keyhole staability |
| Unmelt Model | Predcition of melt pool formation | Determination of complete melting of designed joint volume |

FIG. 5

600

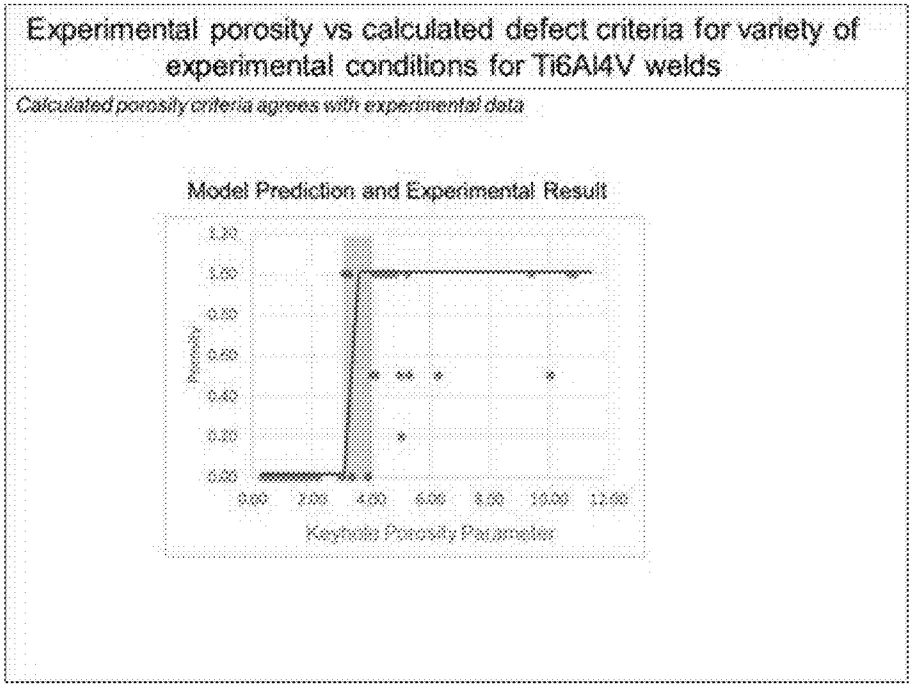

FIG. 6

PREDICTIVE OPTIMIZATION AND CONTROL FOR FUSION WELDING OF METALS

CROSS REFERENCE TO RELATED APPLICATIONS

This application claims the benefit of priority to U.S. Provisional Application No. 63/324,294 filed Mar. 28, 2022, the entire contents of which are incorporated herein by reference thereto.

BACKGROUND

The subject matter disclosed herein generally relates to manufacturing and fabrication and, more particularly, to metal fusion welding processes and techniques.

Welding is the process of joining materials, such as metals or thermoplastics, by using heat. Fusion welding processes make up a large sector of welding and joining processes. In fusion welding, localized heating is applied to the interfaces of two or more sub-components. The interfaces are heated to a temperature above their melting temperature where the liquid from both sub-components flow together and mix to form a molten pool. The molten pool remains in contact with the original sub-components and subsequently re-solidifies after the thermal energy is removed. The solidified material (weld) joins the sub-components together.

The process of fusion welding is complicated by various physical and mechanistic factors, such as geometry of the joint to be produced between two or more details, the thermal mass of the details, the energy and rate of energy input into the adjacent surfaces of the details, and the material that make up the details. These factors lead to specific process reaction and behavior that can lead to sound, defect-free joints or alternatively to joints that have undesired features that may limit the capability of the final joint.

BRIEF DESCRIPTION

According to an embodiment, a method includes receiving weld data about a weld. The method further includes analyzing, using a physics-based model, the weld data to predict a formation of a defect in the weld. The method further includes providing feedback to enable process optimization during a design stage or active control during welding to control a welding machine to correct for and eliminate the formation of the defect in the weld.

In addition to one or more of the features described above or below, or as an alternative, further embodiments may include that receiving the weld data about the weld comprises capturing the weld data about the weld during component and process design.

In addition to one or more of the features described above or below, or as an alternative, further embodiments may include that receiving the weld data about the weld comprises capturing the weld data about the weld using a sensor, wherein the sensor is one or more of a camera, a pyrometer, or a spectrometer.

In addition to one or more of the features described above or below, or as an alternative, further embodiments may include that receiving the weld data about the weld comprises capturing the weld data about the weld from sensors and controls within welding machine.

In addition to one or more of the features described above or below, or as an alternative, further embodiments may include that the sensors and controls within the welding machine comprises a power input, a time of power input, a gas flow rate, or a traverse speed.

In addition to one or more of the features described above or below, or as an alternative, further embodiments may include that the weld data is computationally processed through a series of algorithms to predict steps in a welding process.

In addition to one or more of the features described above or below, or as an alternative, further embodiments may include that the analyzing the weld data comprises analyzing the weld data using algorithms to predict a defect formation.

In addition to one or more of the features described above or below, or as an alternative, further embodiments may include that the predicted defect formation provides input to steps of a design optimization or active control inputs.

In addition to one or more of the features described above or below, or as an alternative, further embodiments may include that the design optimization is conducted by automated routines or by manual assessment of parameters based on a design and process constraint.

In addition to one or more of the features described above or below, or as an alternative, further embodiments may include that the design and process constraint comprises one or more of a weld joint geometry, power settings, and a total power input.

In addition to one or more of the features described above or below, or as an alternative, further embodiments may include that the active control during welding is conducted by analysis of instantaneous sensor measurements and prediction of weld stability.

In addition to one or more of the features described above or below, or as an alternative, further embodiments may include that welding machine is a robotic welding machine.

In addition to one or more of the features described above or below, or as an alternative, further embodiments may include that robotic welding machine includes control system algorithms to perform defect prediction based on sensor data.

In addition to one or more of the features described above or below, or as an alternative, further embodiments may include that robotic welding machine actively calculates stability of instantaneous weld conditions and autonomously adjusts parameters to maintain stability and defect-free welds.

In addition to one or more of the features described above or below, or as an alternative, further embodiments may include that a laser power at a weld start is gradually increased.

In addition to one or more of the features described above or below, or as an alternative, further embodiments may include that a laser power at a weld stop is gradually decreased.

Other embodiments described herein implement features of the above-described method in computer systems and computer program products.

The above features and advantages, and other features and advantages, of the disclosure are readily apparent from the following detailed description when taken in connection with the accompanying drawings.

BRIEF DESCRIPTION OF THE DRAWINGS

The following descriptions should not be considered limiting in any way. With reference to the accompanying drawings, like elements are numbered alike:

FIG. 5 depicts a table of example models/criteria according to one or more embodiments described herein;

FIG. 6 depicts a graph of porosity according to one or more embodiments described herein;

DETAILED DESCRIPTION

Figure 1:
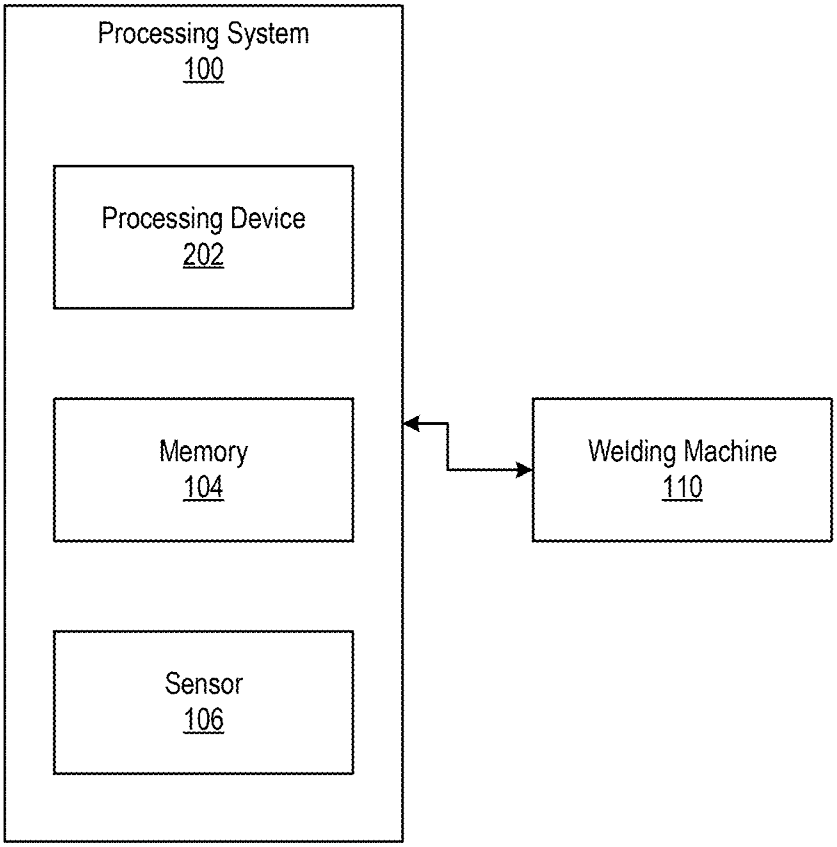
FIG. 1 is a block diagram of a system for implementing one or more embodiments described herein.

A detailed description of one or more embodiments of the disclosed algorithms, apparatus, system, and method are presented herein by way of exemplification and not limitation with reference to the Figures.

As described herein, the process of fusion welding is complicated by various physical and mechanistic factors. These factors lead to specific process reaction and behavior that can cause some joints to include defects. Understanding the interactions between the various parameters within the welding process and the associated physics-based mechanisms for heat transfer, fluid flow, phase change from both a thermodynamic and kinetics perspective enable the optimal design and control of welding processes. One or more embodiments described herein provides a framework and associated computational tools to predict the outcome of welding processes from arbitrary geometries, materials systems, and welding parameters.

Welding is one of the oldest manufacturing processes, where two or more sub-components are jointed. Fusion welding processes comprise a large sector of welding and joining processes. In fusion welding, localized heating is applied to the interfaces of two or more sub-components. The interfaces are heated to a temperature above their melting temperature where the liquid from both sub-components flow together and mix. The molten pool remains in contact with the original sub-components and subsequently re-solidifies after the thermal energy is removed. The solidified material (weld) joins the sub-component together. The mechanical properties of the weld are largely controlled by how the material is melted and solidified during the welding process. Uncontrolled welding processes lead to weld defects such as porosity, or unmelted regions (lack of penetration) or other melting and solidification features. Porosity typically occurs if the supplied energy is too high, unmelted regions (lack of penetration) typically occurs if supplied anergy is too low. The supplied energy increases with laser beam power density and decreases with the beam speed. Defects can also be generated at start and stop of welding when the laser is turned on or off when the beam sped is equal to zero and laser energy is not. The weld defects often result in local stress concentrations and nucleation sites for crack initiation and/or propagation, making these features highly undesirable. A modeling technology has been developed that can provide accurate prediction of defect formation based on the processing path utilized to produce the defect free high quality weld. This technology can be used to plan welding processes or can be used as a means of active, adaptive controls.

One or more embodiments described herein provide for designing and controlling fusion welding processes to provide for elimination of undesirable defects and features. One or more embodiments described herein can increase the speed at which weld process designs can be developed and optimized virtually instead of by physical trial and error approaches. Additionally, one or more embodiments described herein can be applied to control systems for closed-loop controls that ensure safe manufacture of welds. Conventional approaches to welding processes do not provide a predictive approach for optimization or for closed-loop control based on specific welding feature or defect elimination.

One or more embodiments described herein can be applied to substantially automated and robotically controlled welding processes. One or more embodiments described herein captures the physics of what is occurring during melting and solidification and provides a direct, local feedback regarding success of the weld at the point (locally) being welded.

One or more embodiments described herein provide a modeling approach that can provide accurate prediction of defect formation of a weld based on the processing path utilized to produce the weld. This approach can be used to plan welding processes and/or to control (e.g., using a closed-loop control process) a welding machine by providing active, adaptive controls to perform the welding operation.

The computational modeling framework can include a series of sub-models or algorithms that take material and process boundary conditions and predict outputs for the various elements or steps in the welding process. The sub-models are arranged and linked together to enable an overarching prediction of the quality of the weld relative to whether various features are predicted to occur in the final weld.

According to one or more embodiments described herein, one or more sub-models include, but are not limited to: a thermal model, a mechanical model, a melt pool and fluid flow model, and a solidification model. The thermal model can include one or more algorithms that calculate spatial and temporal changes in temperature at instances of the welding process. The thermal model is also linked to other sub-models, which provide input information and are receivers of output information from the thermal model. The mechanical model provides for prediction of physical changes in the input details and the joined assembly as a function of local and global thermal expansion from the welding heat input. The melt pool and fluid flow model predicts the size, shape, and liquid flow within the melt pool. The solidification model provides prediction of solidification path, shrinkage porosity, and welding induced stresses.

Although welding processes have been studied previously, no known predictive approach for optimization and/or for closed-loop control based on specific welding features or defect elimination exists. One or more embodiments described herein can be applied to substantially automated and robotically controlled welding processes. One or more embodiments described herein captures the physics of what is occurring during melting and solidification and provides a direct, local feedback regarding success of the weld at the point (locally) being welded.

One or more embodiments described herein have the advantage of increasing the speed at which weld process designs can be developed and optimized virtually instead of by conventional physical trial and error approaches. Additionally, one or more embodiments described herein can be applied to control systems for closed-loop controls that ensure safe manufacture of welds.

One or more embodiments described herein provide for making estimates and identifying key processes and factors that capture major physics before building the model. One or more embodiments described herein derive new/identify equations governing the key processes focusing on appropriate fidelity level. One or more embodiments described herein solve governing equations for different scales analytically, if possible, or obtain approximate analytical solution or course grained solution. One or more embodiments described herein provide a combined multi-scale analytical/numerical approach that enables computation acceleration by orders of magnitudes as compared with straightforward approaches. One or more embodiments described herein implement the model into the fast acting modeling tool with user friendly interface and incorporate into design tool.

Referring now to FIG. 1, a system 100 for implementing one or more embodiments described herein. The system 100, which can be referred to as a processing system, includes a processing device 102 (e.g., a processor, multiple processors, etc.), a memory 104 (e.g., a random access memory (RAM), a read-only memory (ROM), etc., including combinations thereof), and a sensor 106 (e.g., a camera, a LIDAR sensor, an infrared sensor, etc.).

The system 100 can be communicatively connected to a welding machine 110. According to one or more embodiments described herein, the system 100 can receive data (e.g., information) from the welding machine 110 and can transmit data (e.g., commands) to the welding machine 110 to control operation of the welding machine, such as to correct a defect in a weld.

Figure 2:
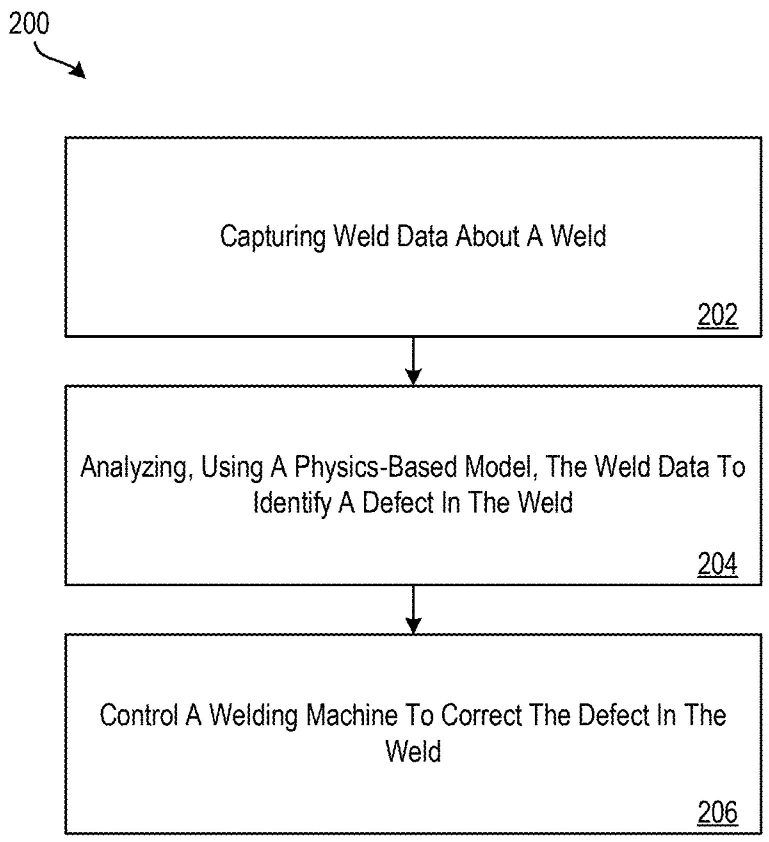
FIG. 2 is a flow diagram of a method for implementing one or more embodiments described herein.

The features and functionality described herein regarding the method of FIG. 2 can be implemented as instructions stored on a computer-readable storage medium, as hardware modules, as special-purpose hardware (e.g., application specific hardware, application specific integrated circuits (ASICs), application specific special processors (ASSPs), field programmable gate arrays (FPGAs), as embedded controllers, hardwired circuitry, etc.), or as some combination or combinations of these. According to aspects of the present disclosure, the features and functionality described herein can be a combination of hardware and programming. The programming can be processor executable instructions stored on a tangible memory, and the hardware can include the processing device 102 for executing those instructions. Thus a system memory (e.g., memory 104) can store program instructions that when executed by the processing device 102 implement the engines described herein. Other engines can also be utilized to include other features and functionality described in other examples herein.

The processing system 100 can be used to generate a model to analyze welds to provide a predictive approach for optimization of the welds and/or for closed-loop control based on specific welding features or defect elimination. For example, an artificial intelligence approach, such as machine learning, can be implemented such that training data is used to train a model to analyze welds to identify defects. As another example, an analytical model(s) can be generated that are calibrated and validated for the material and processing space for particular applications.

Referring now to FIG. 2 with continued reference to FIG. 1, FIG. 2 is a flow chart illustrating a method 200 according to one or more embodiments described herein. The method 200 may be performed, for example, by the processing system 100 of FIG. 1 or another suitable system and/or device.

At block 202, the processing system 100 receives data about a weld. For example, the processing system captures data about a weld using the sensor 106. In an example in which the sensor 106 is a camera, the camera can capture an image (or images) of a weld. Such images can be automatically analyzed for both weld pool temperature and shape/size, which can be compared with the predicted values. Variations beyond a set value indicate a deviation in the desired process and need for process correction. A control system (e.g., the processing system 100 or another suitable system) can obtain feedback from the prediction algorithms regarding which parameters to change, including direction and magnitude. Continued monitoring and sensor feedback can be further analyzed to confirm return to desired control state.

At block 204, the processing system 100 analyses, using a physics-based model, the weld to predict a formation of a defect in the weld. Examples of key characteristics include melt pool temperature, melt pool shape, and/or geometry characteristics of the melt pool key hole and the like. It should be appreciated that the physics-based model does not require time-consuming simulations and extensive experimental calibration. The physics-based model provides the following capabilities and features: calculation of process map to provide visualization of defect free/rich areas in laser power and scanning rate cross-section of multiple parameter spaces; calculation of 2D and 3D defect maps from first-principles with no empirical calibration being used; and calculation of a 3D defect map for simple geometry is much faster (e.g., 40×) than for more complicated geometries.

With reference to FIG. 5, a table 500 of example models/criterion is depicted according to one or more embodiments described herein. In this example, the following models/criterion are shown: a Marangoni-based flow model, a keyhole onset criterion, a keyhole stability criterion, and an unmelt model. It should be appreciated that these models/criterion are merely examples, and that additional, fewer, and/or other models and/or criteria can be implemented according to one or more embodiments described herein. Each of the models/criteria of the table 500 have an associated function and output as shown. For example, the Marangoni-based flow model provides a function of "prediction of flow and temperature profile in melt pool" and provides an output of "local temperature in melt pool." The keyhole onset criterion provides a function of "definition of when keyhole features form" and provides an output of "criterion value for keyhole formation." The keyhole stability (or "instability") criterion provides a function of "definition of when keyhole is stable" and provides an output of "criterion value for keyhole stability. The unmelt model provides the function of "prediction of melt pool formation" and provides an output of "determination of complete melting of designed joint volume."

With continued reference to FIG. 2, the physics-based model can be used to identify multiple types of defects, which can include a regular unmelt/porosity defect, a keyhole/porosity defect, and/or a non-regular (fluctuation unmelt) defect. A non-regular defect would be when there is variation in component detail geometry(ies) that result in variations that are not planned or necessarily desired, but as a result of variation in weld join geometry. Analytical equations for defect onset are used, such as P=f(V,T) where T is temperature in vicinity of a laser beam that depends on thermal history and also on welding pattern such as wobbling. According to one or more embodiments described herein, local temperature in vicinity of laser beam is calculated through analytical/numerical multi-scale approach. Part geometry and hatching algorithm can be taken into account.

At block 206, defects can be corrected. For example, the processing system 100 can provide feedback to enable process optimization during the design stage or active control during welding to control the welding machine 110 to correct for and eliminate the formation of the defect in the weld.

While the above description has described the flow process of FIG. 2 in a particular order, it should be appreciated that unless otherwise specifically required in the attached claims that the ordering of the steps may be varied.

Figure 4:
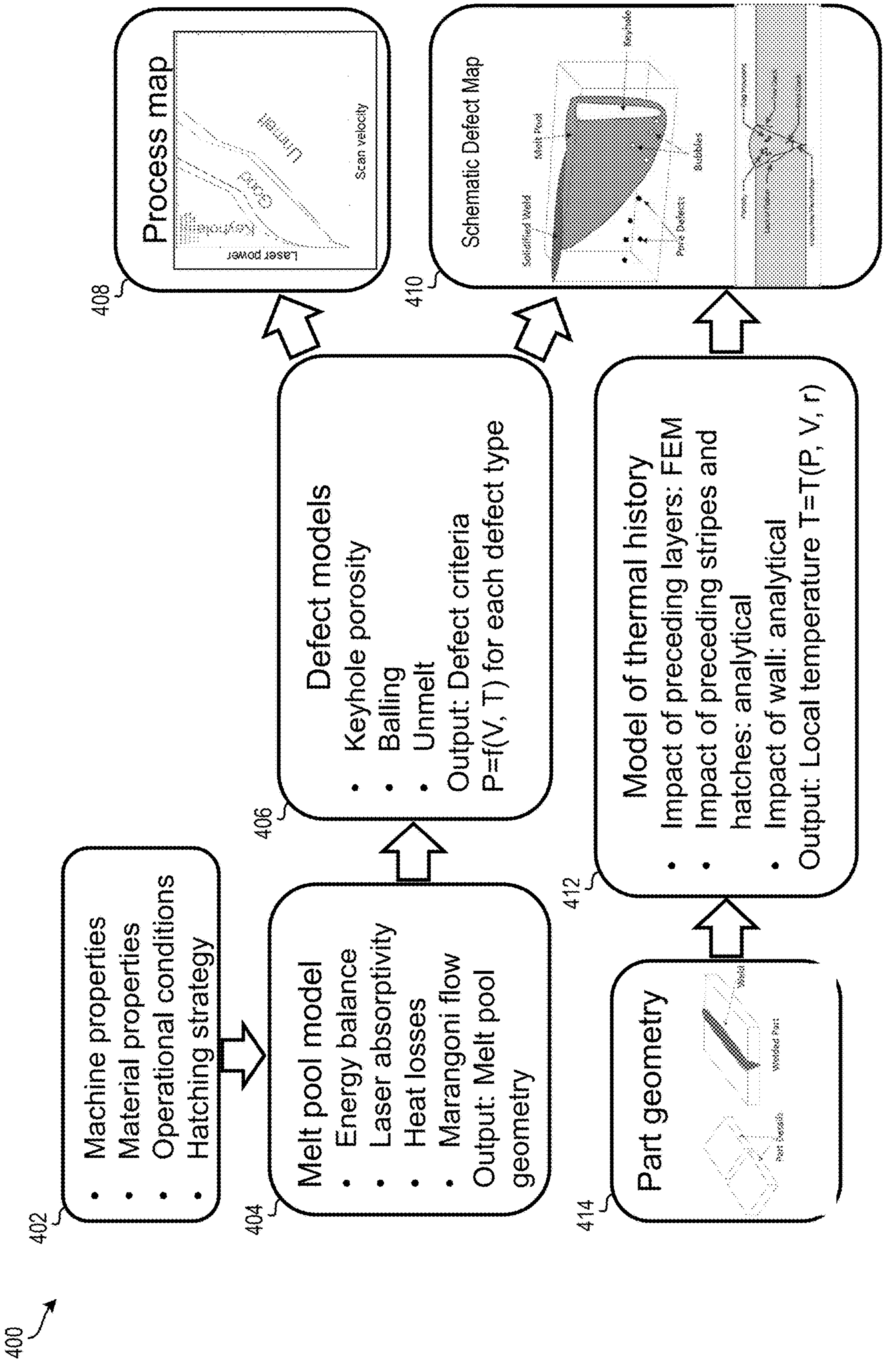
FIG. 4 depicts a flow diagram of a method for implementing one or more embodiments described herein.

FIG. 4 depicts a block diagram of a method 400 according to one or more embodiments described herein. The method 400 can be implemented using any suitable device or system such as the processing system 100 of FIG. 1. At block 402, the processing system 100 receives and/or captures data, which may include machine properties, material properties, operational conditions, and/or hatching strategy.

At block 404, the processing system 100 applies a melt pool model that takes as input energy balance, laser absorptivity, heat losses, and/or Marangoni flow and generates a melt pool geometry as output, which is fed into defect models at block 406. As an example, the defect models take as inputs keyhole porosity, balling, and unmelt and generate as output a defect criteria (P=f(V,T)) as described herein for each defect type. For example, with reference to FIG. 6, a graph 600 is shown of experimental porosity versus calculated defect criteria for a variety of experimental conditions for a Ti6Al4V weld type. As shown, the calculated porosity criteria agrees with the experimental data.

Figure 7:
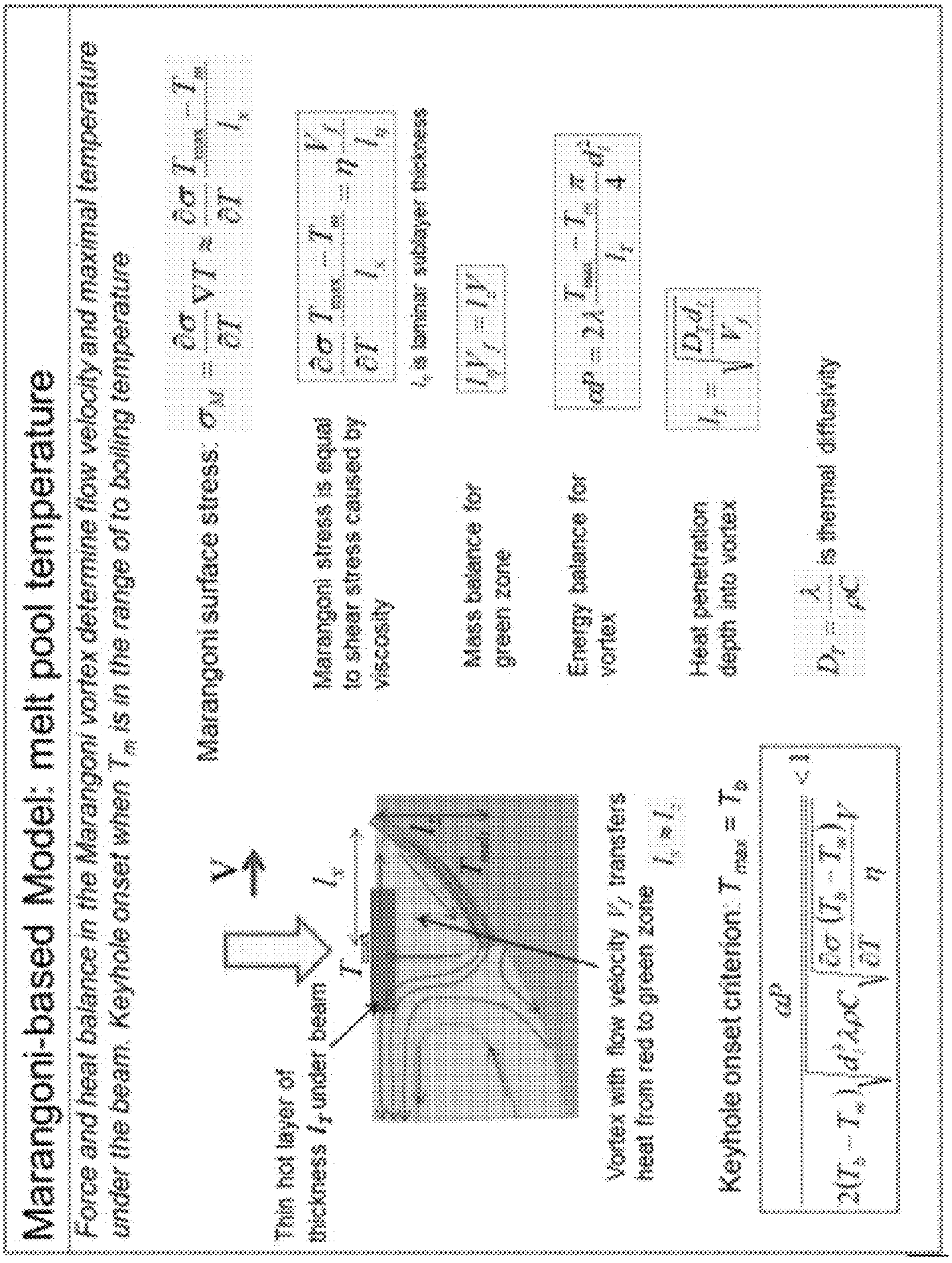
FIG. 7 is a graphical representation of a Marangoni-based model according to one or more embodiments described herein.

As another example, FIG. 7 depicts a graphical representation 700 of a Marangoni-based model according to one or more embodiments described herein. The Marangoni-based flow model provides a function of "prediction of flow and temperature profile in melt pool" and provides an output of "local temperature in melt pool." In the Marangoni-based model, force and heat balance in the Marangoni vortex determine flow velocity and maximal temperature under the beam. A keyhole onset occurs when $T_m$ is in the range of boiling temperature.

Figure 8:
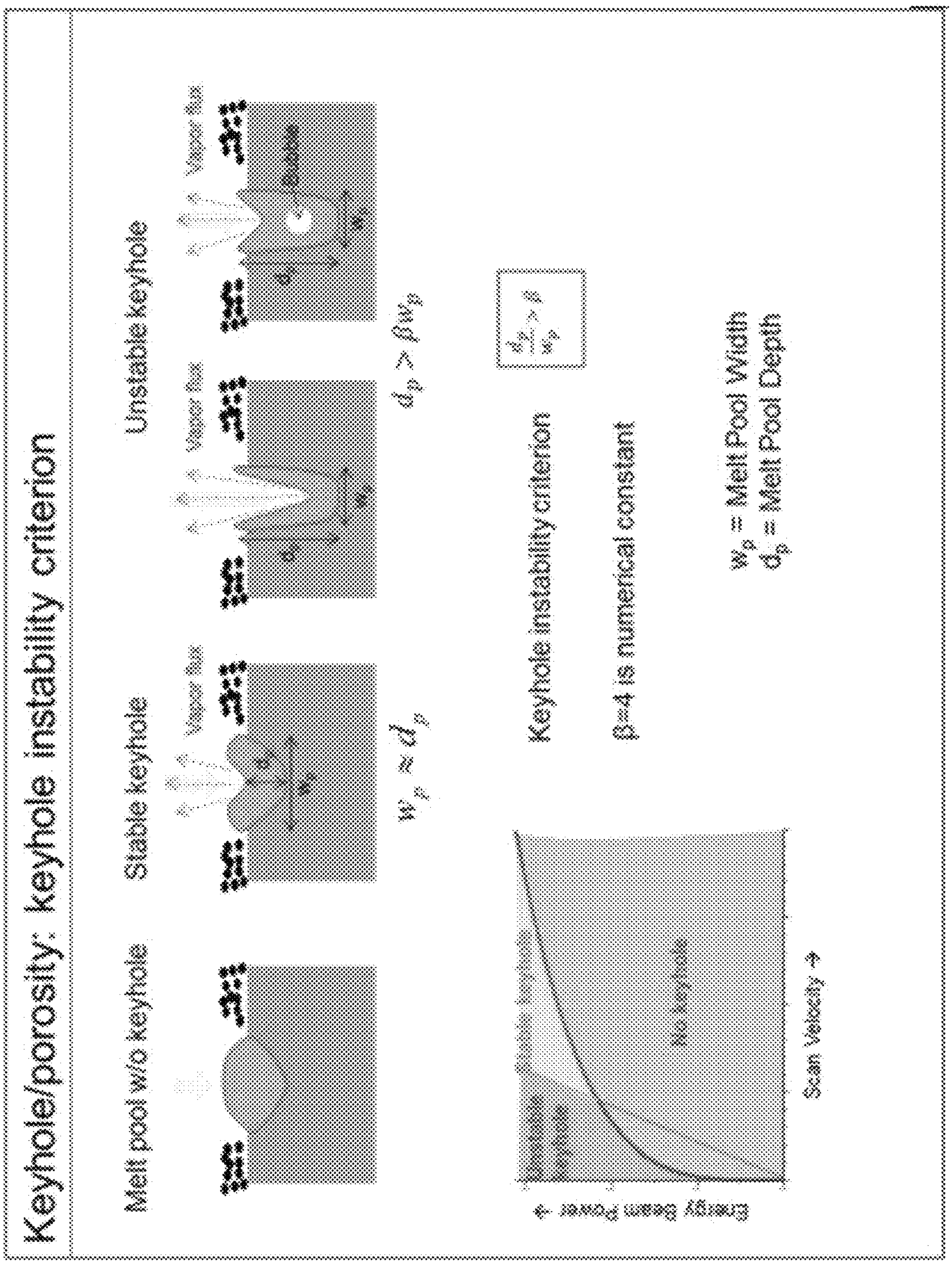
FIG. 8 is a graphical representation of a keyhole porosity formation criterion according to one or more embodiments described herein.

As another example, FIG. 8 depicts a graphical representation 800 of a keyhole stability (i.e., instability) criterion according to one or more embodiments described herein. The keyhole stability criterion provides a function of "definition of when keyhole is stable" and provides an output of "criterion value for keyhole stability.

Figure 3:
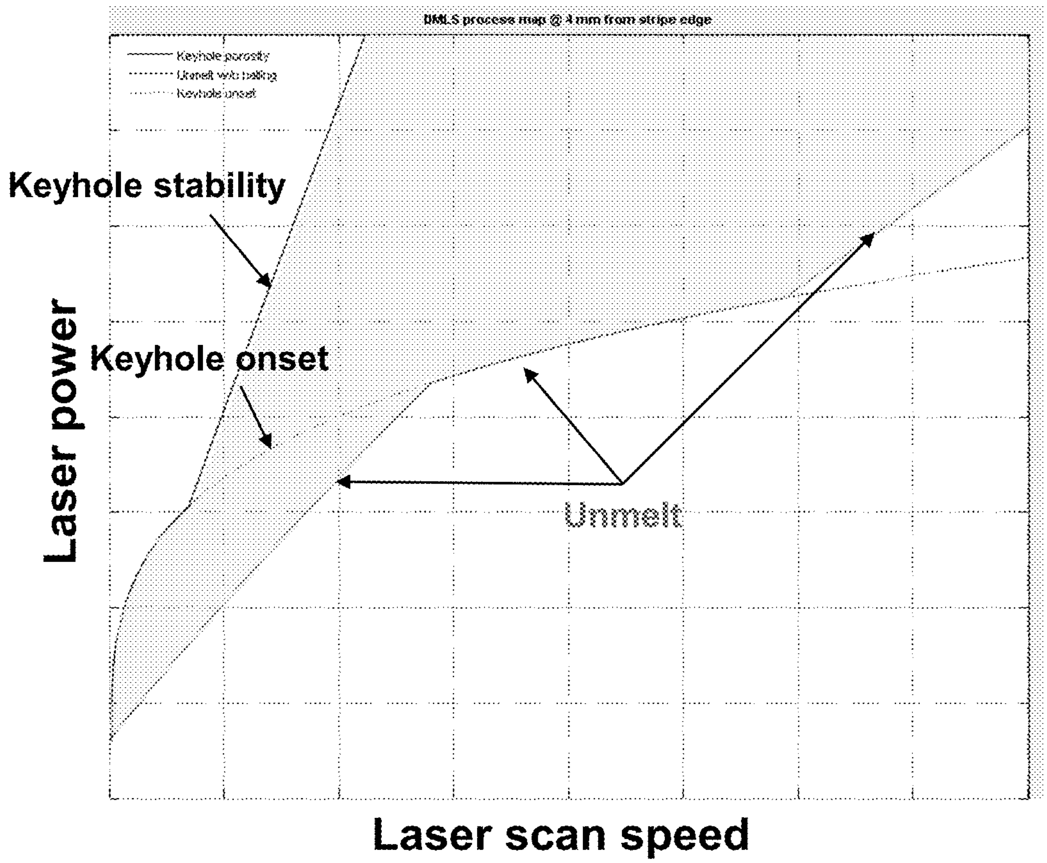
FIG. 3 depicts a process map according to one or more embodiments described herein.

With continued reference to FIG. 4, the outputted defect criteria are used to generate a process map 408 (see, e.g., the process map 302 of FIG. 3).

The defect maps are also created and/or updated/improved using a model of thermal history at block 412 using part geometry 414. Particularly, the model of thermal history takes as input the impact of preceding layers, the impact of preceding stripes and hatches, and the impact of the wall and generates an output the local temperature (T=T(P,V,r)).

According to one or more embodiments described herein, input into the method 400 can be achieved using a flexible model interface that enables to download arbitrary part geometry from a file (such as an STL file), operational conditions from a user interface, machine properties and material properties from user created text files, and the like. This provides for the method 400 to work with arbitrary part geometry and arbitrary material.

According to one or more embodiments described herein, the output of the method 400 can be in the form of the process map 408 and/or the defect maps 410. The process map 408 provides analytical defect onset criteria P(V,T) for fixed T results in process map and the process map provides for a user to choose defect free processing window. The defect maps 410 depict that local undercooling results in local unmelt while local overheating results in local keyhole in the same cross-section.

According to one or more embodiments described herein, the laser power at a weld start is gradually increased. According to one or more embodiments described herein, the laser power at a weld stop is gradually decreased. This can be correlated with a gradual increase or decrease of the beam speed so that the power density P is contained in the limits predicted by the model for defect free operation.

Figure 9A:
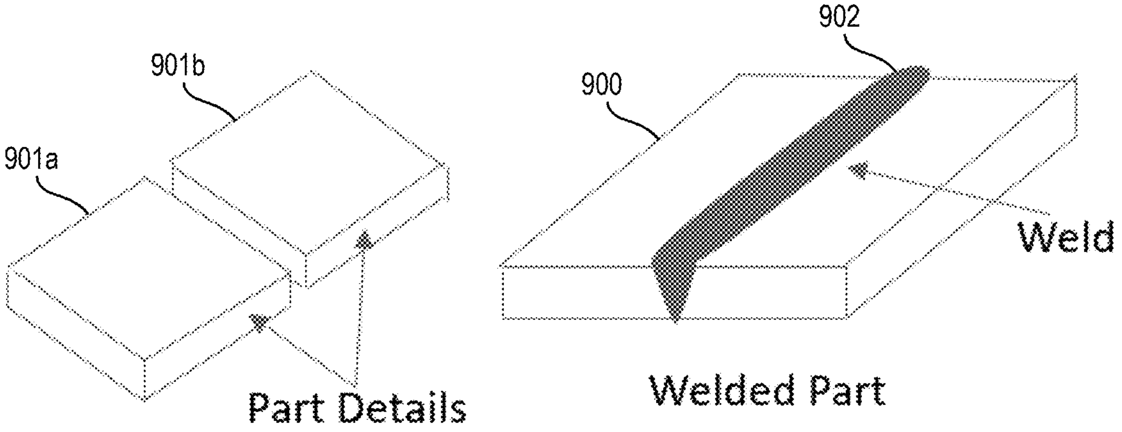
FIG. 9A is a graphical representation of a welded part according to one or more embodiments described herein.
Figure 9B:
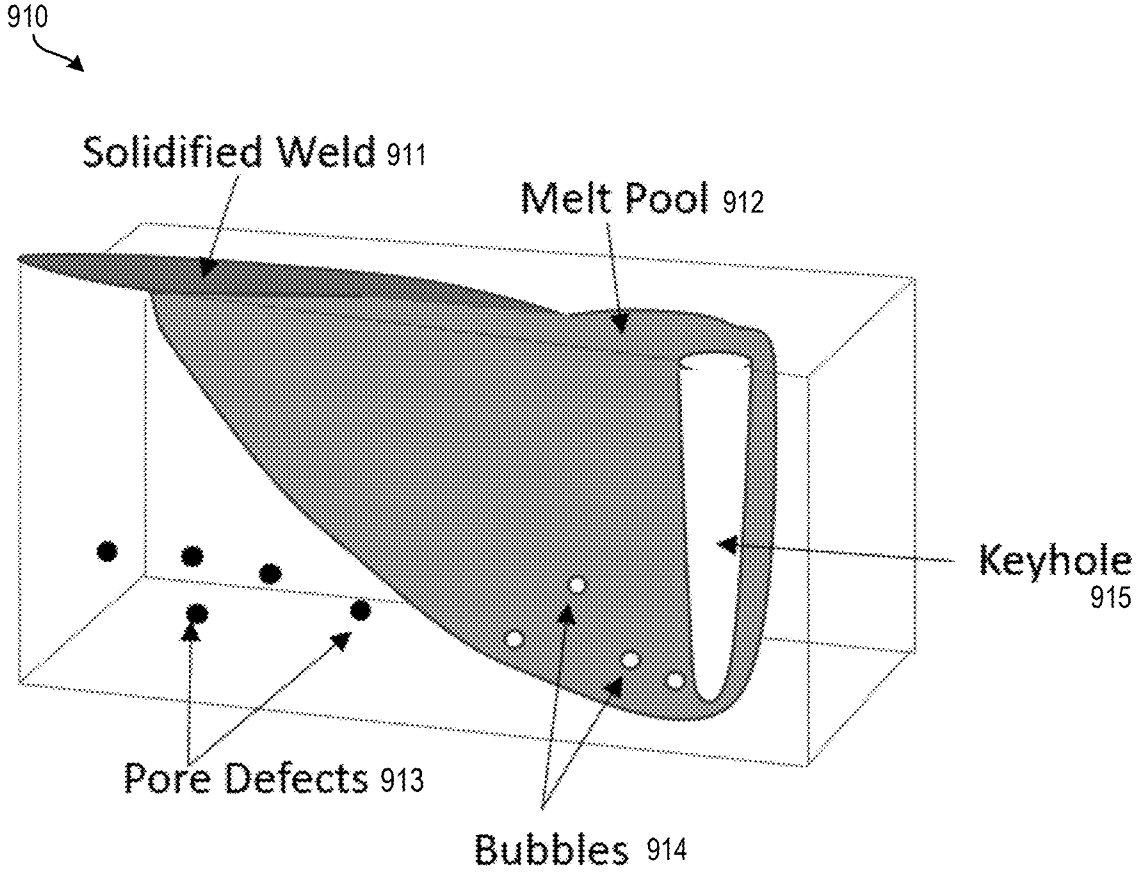
FIG. 9B is a graphical representation of a defect map according to one or more embodiments described herein.

FIG. 9A is a graphical representation of a welded part 900 according to one or more embodiments described herein. In particular, the welded part 900 is formed by welding together two separate parts 901*a*, 901*b* using a weld 902 as described herein. FIG. 9B is a graphical representation of a defect map 910 of the weld 902 of the welded part 900 according to one or more embodiments described herein. In this example, the solidified weld 911 and melt pool 912 are formed during the weld. Defects are shown as pore defects 913, bubbles 914, and a keyhole 915.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A method comprising:

receiving weld data about a weld;

analyzing, using a physics-based model, the weld data to predict a formation of different types of defects in the weld and identify a formation of the different types of defects in the weld; and providing feedback to enable process optimization during a design stage or active control during welding to control a welding machine to correct for and eliminate the formation of an identified defect in the weld among the different types of defects.

2. The method of claim 1, wherein receiving the weld data about the weld comprises capturing the weld data about the weld during component and process design.

3. The method of claim 2, wherein the weld data is computationally processed through a series of algorithms to predict steps in a welding process.

4. The method of claim 2, wherein the analyzing the weld data comprises analyzing the weld data using algorithms to predict a defect formation.

5. The method of claim 4, wherein the predicted defect formation provides input to steps of a design optimization or active control inputs.

6. The method of claim 5, wherein the design optimization is conducted by automated routines or by manual assessment of parameters based on a design and process constraint.

7. The method of claim 6, wherein the design and process constraint comprises one or more of a weld joint geometry, power settings, and a total power input.

8. The method of claim 2, wherein the active control during welding is conducted by analysis of instantaneous sensor measurements and prediction of weld stability.

9. The method of claim 1, wherein receiving the weld data about the weld comprises capturing the weld data about the weld using a sensor, wherein the sensor is one or more of a camera, a pyrometer, or a spectrometer.

10. The method of claim 9, wherein receiving the weld data about the weld comprises capturing the weld data about the weld from sensors and controls within welding machine.

11. The method of claim 10, wherein the sensors and controls within the welding machine comprises a power input, a time of power input, a gas flow rate, or a traverse speed.

12. The method of claim 1, wherein welding machine is a robotic welding machine.

13. The method of claim 12, wherein robotic welding machine includes control system algorithms to perform defect prediction based on sensor data.

14. The method of claim 12, wherein robotic welding machine actively calculates stability of instantaneous weld conditions and autonomously adjusts parameters to maintain stability and defect-free welds.

15. The method of claim 1, wherein a laser power at a weld start is gradually increased.

16. The method of claim 1, wherein a laser power at a weld stop is gradually decreased.

* * * * *